(12) United States Patent
Lo

(10) Patent No.: US 9,492,155 B2
(45) Date of Patent: Nov. 15, 2016

(54) SECURING ELEMENT

(76) Inventor: Kokbing Lo, Oldenzaal (NL)

( * ) Notice: Subject to any disclaimer, the term of this patent is extended or adjusted under 35 U.S.C. 154(b) by 499 days.

(21) Appl. No.: 11/816,512

(22) PCT Filed: Feb. 16, 2006

(86) PCT No.: PCT/NL2006/000080
§ 371 (c)(1),
(2), (4) Date: May 5, 2008

(87) PCT Pub. No.: WO2006/088359
PCT Pub. Date: Aug. 24, 2006

(65) Prior Publication Data
US 2008/0288070 A1 Nov. 20, 2008

Related U.S. Application Data

(60) Provisional application No. 60/658,742, filed on Mar. 7, 2005.

(30) Foreign Application Priority Data

Feb. 16, 2005 (NL) ..................................... 1028292

(51) Int. Cl.
*A61F 2/08* (2006.01)
*A61B 17/04* (2006.01)

(52) U.S. Cl.
CPC ......... *A61B 17/0401* (2013.01); *A61F 2/0811* (2013.01); *A61B 2017/045* (2013.01); *A61B 2017/0414* (2013.01); *A61F 2002/0829* (2013.01); *A61F 2002/0864* (2013.01); *A61F 2002/0882* (2013.01); *A61F 2250/0073* (2013.01)

(58) Field of Classification Search
CPC ........................... A61F 2/0811; A61B 17/0401
USPC .......... 623/13.13–13.14, 13.11–13.12, 13.15, 623/13.2; 606/232
See application file for complete search history.

(56) References Cited

U.S. PATENT DOCUMENTS

| 4,828,562 | A | | 5/1989 | Kenna |
| 4,950,271 | A | * | 8/1990 | Lewis et al. .................. 606/102 |
| 5,192,287 | A | * | 3/1993 | Fournier et al. .............. 606/139 |

(Continued)

FOREIGN PATENT DOCUMENTS

| DE | 20220911 U1 | 6/2004 |
| WO | 9736557 A1 | 10/1997 |
| WO | 0156507 A1 | 2/2001 |

*Primary Examiner* — Marcia Watkins
(74) *Attorney, Agent, or Firm* — Browdy and Neimark, PLLC

(57) ABSTRACT

A securing element is intended for connecting a ligament to a bone part of a human or animal. The securing element comprises a wire or thread which is intended to be connected to the ligament. A clamping element of the securing element clamps' at least one part of the wire or thread in a releasable manner, for which purpose the clamping element comprises a first clamping part and a second clamping part. The first clamping part is provided with a conical first surface and the second clamping part is provided with a corresponding conical second surface on a side facing the first clamping part, in order for the at least one part of the ligament coupling element to be clamped between the first and second surfaces. The clamping element can be actuated from outside the body.

15 Claims, 3 Drawing Sheets

(56) References Cited

U.S. PATENT DOCUMENTS

| | | | |
|---|---|---|---|
| 5,356,435 A | 10/1994 | Thein | |
| 5,702,397 A | 12/1997 | Goble et al. | |
| 5,964,764 A | 10/1999 | West, Jr. et al. | |
| 5,980,473 A * | 11/1999 | Korakianitis et al. | 600/587 |
| 6,036,694 A * | 3/2000 | Goble et al. | 606/304 |
| 6,517,542 B1 * | 2/2003 | Papay et al. | 606/232 |
| 6,997,189 B2 * | 2/2006 | Biggs et al. | 128/898 |
| 7,875,056 B2 * | 1/2011 | Jervis et al. | 606/232 |
| 2005/0065533 A1 * | 3/2005 | Magen et al. | 606/102 |

* cited by examiner

SECURING ELEMENT

The invention relates to a securing element for connecting a ligament to a bone part of a human or animal.

A ligament, such as a joint ligament, in the body of a human or animal can be damaged by overloading (such as excessive tensile force) or other causes, for example can tear or lose its attachment to a bone. It is possible to surgically replace the damaged ligament by a new ligament, in which case it is possible to use ligament material which has been removed from a different site in the body or an artificial material. The new ligament then has to be secured at its ends to a respective associated bone part with the aid of suitable securing elements.

The prior art has proposed various types of securing elements, such as a screw with or without a toothed ring, a clip or staple, a bone plug, a toothed plug, a button-like element ("endo-button") or the like.

U.S. Pat. No. 5,702,397 discloses a securing element having a clamping element which comprises an elongate body to be secured in a tunnel in a bone. In its longitudinal direction, the body is provided with a through hole which is partially tapering, and has a circular cross-section. One or more sutures or shafts connected to a ligament can be threaded through the hole. The one or more sutures or shafts are clamped against the inner surface of the hole by means of a movable clamping part, e.g. shaped as a ball having a diameter which is smaller than the largest diameter of the hole, and which is larger than the smallest diameter of the hole. A spring force can be exerted on the ball to increase the clamping. After setting a mechanical traction force and a required length of the one or more sutures or shafts in this way, the excess, non-operative part of the sutures or shafts is cut off.

Although a natural or artificial ligament, during the surgical intervention of putting it in place, can be placed under a satisfactory tension for use, after some time it is irreversibly stretched in use, and also a slippage between the suture or shaft and the clamping element may occur, and these effects usually cause the patient to suffer reduced function, pain and instability. The patient runs the risk of damage to a joint where the new ligament is used, with an increasing degree of degeneration and/or osteoarthritis in the joint. There is therefore a need for a ligament securing means with which the tension in the ligament can be set and readjusted.

A securing element which can specifically be set and readjusted is known from NL-C-1 005 394. This publication shows a securing element which is intended to secure a ligament which has been fitted through a hole in a joint part at one end of said ligament, it being possible to vary the tensile stress acting on the tendon by varying the position of anchoring of an element which acts on the ligament. To this end, a cylindrical element provided with an external profile is stably secured in bone material, adjacent to a channel in which a new ligament is to be arranged. The ligament is composed of a large number of fibres which are securely clamped in a cylindrical clamping block. The clamping block can be moved a short distance in the axial direction (i.e. in the longitudinal direction of the ligament) within a sleeve, which is in turn externally connected to the cylindrical element by means of a screw connection; for this purpose, the cylindrical element is provided with an internal screw thread. On its side facing towards the channel, the clamping block is supported on the sleeve by means of a compression spring. The tension in the ligament can be varied by rotating the sleeve, while the tension in the ligament can be kept at virtually the same level in the event of minor changes in length of the ligament by the action of the spring. The rotation of the sleeve for varying the tension in the ligament can be done directly after providing the securing element in the body, but also some time later. For this readjustment, it is necessary to gain access again to the securing element in the body through surgery.

A drawback of the securing element which is known from NL-C-1005394 is its complicated construction, which comprises a number of components that have to be produced with a high degree of accuracy.

Another drawback is the time required to fit the securing element in the body and then set it appropriately. For a setting afterwards (readjusting) again an invasive surgery must be performed, which is time-consuming, increases the risk of infection, is burdensome for the patient, and prolongs the recovery time.

Another significant drawback is the difficulty of controlling the tension in the ligament which can be effected using the securing element. When the sleeve in the cylindrical element is rotated, it is not possible to measure the change in tension on the ligament, and consequently this change can only be established on a qualitative basis. Also, the degree of compression of the spring cannot be (fully) ascertained during rotation of the sleeve in the cylindrical element, making the effectiveness of the spring dubious. Specifically, since a new ligament will tend to stretch irreversibly after initial use and to slip relative to the securing element, the spring generally has to have a certain prestress, which can absorb the increase in the length of the ligament which occurs over the course of time, during fitting of the ligament. The surgeon performing the operation of fitting the ligament therefore has only very limited options for setting and readjusting an optimum tension in the ligament.

It is an object of the invention to provide a securing element for connecting a ligament to a bone part of a human or animal which can be readjusted in an effective way.

In one embodiment, the securing element according to the invention comprises a ligament coupling element in wire, thread or ribbon form, which is intended to be connected to the ligament; and a clamping element for securely clamping at least one part of the ligament coupling element, the clamping effected by the clamping element being releasable, as described in the claims. A securing element of this type permits the length of the ligament coupling element between the clamping element and the ligament to be varied, in order thereby to allow the ligament to be set to an accurately predetermined tension. This can take place both during an operation for introducing the ligament and at a later stage. In the later stage, invasive surgery is unnecessary for varying the length of the ligament. This possibility of setting and readjustment is particularly advantageous for the patient, since it is thereby possible to ensure correct functioning of the ligament over a prolonged period of time.

In a further embodiment of the securing element according to the invention, the clamping element comprises a first clamping part and a second clamping part, the first clamping part being provided with a first surface and the second clamping part being provided with a corresponding second surface on a side facing the first clamping part, in order for the at least one part of the ligament coupling element to be clamped between the first and second surfaces. The dimensions, orientation and surface properties of the first and second surfaces can easily be selected so as to effect optimum clamping of the ligament coupling element, taking account of the direction of the forces exerted on the clamping element by the ligament coupling element when the ligament is in use. It is preferable for the first and second surfaces to be conical, so that a self-locking function can be obtained.

The text which follows provides a detailed explanation of the invention with reference to a non-limiting exemplary embodiment and a non-limiting example of a method; in the drawings.

Throughout the various figures, the same reference numerals relate to the same components or components with a similar function.

Figure 1:
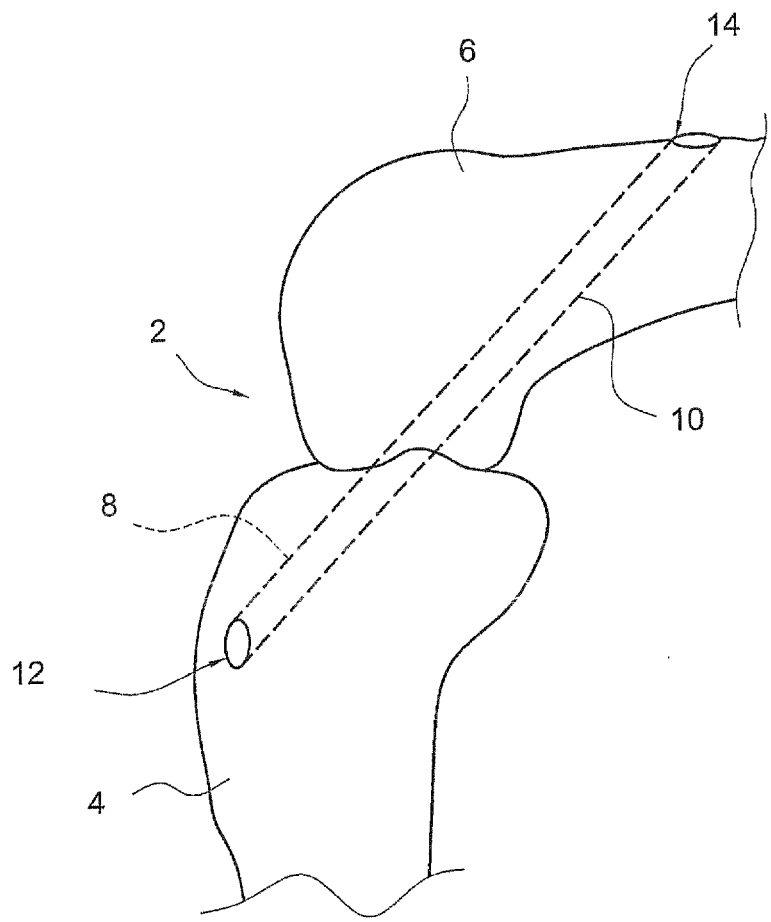
FIG. 1 shows a perspective view of two bone parts.
Figure 2:
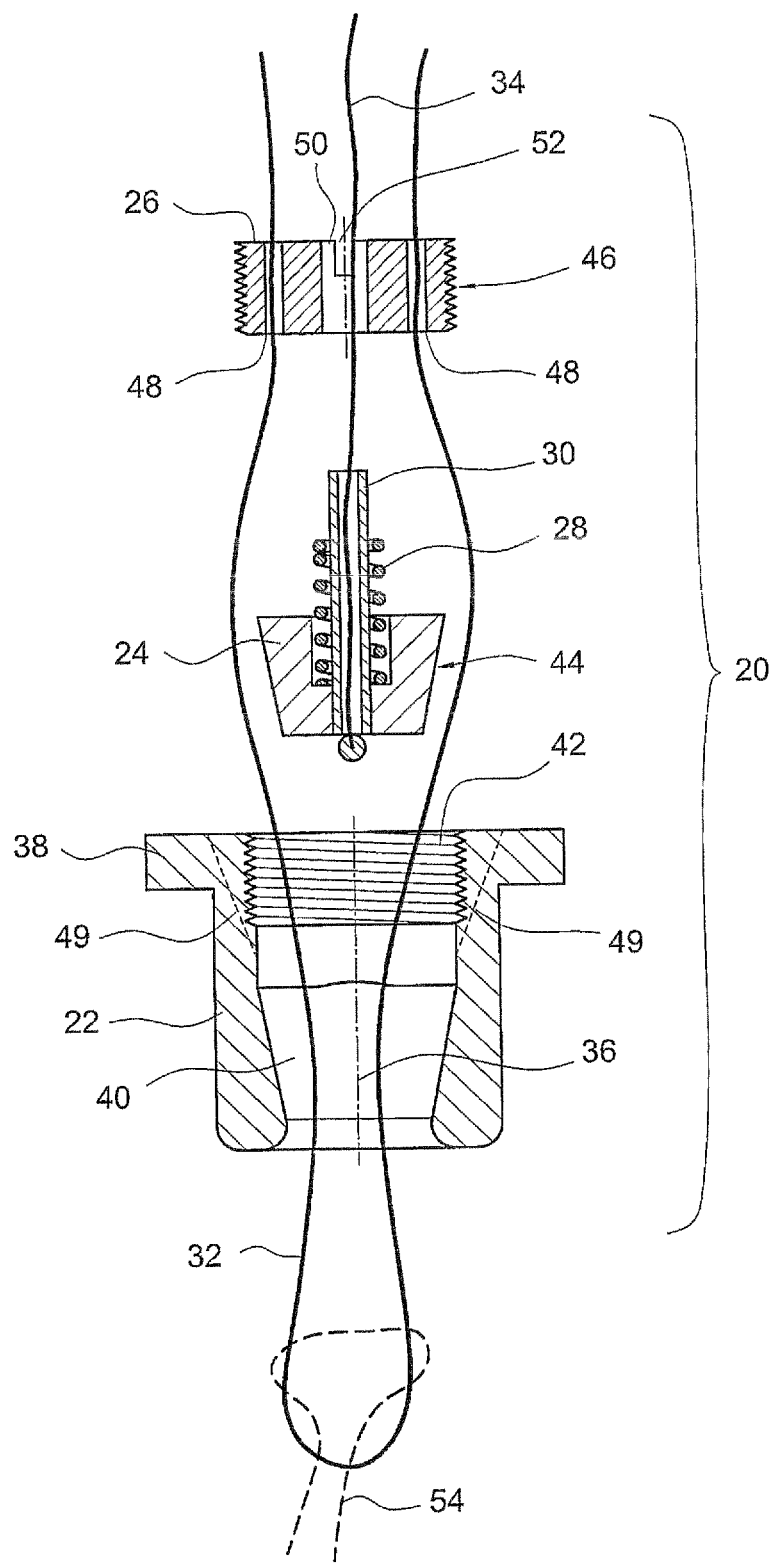
FIG. 2 shows an embodiment of a securing element according to the invention in exploded form on a larger scale in cross section and partially in elevation.

FIG. 1 shows a knee joint 2 of a human body. Through-holes 8 and 10, respectively, which are intended to accommodate a new ligament, have been formed in a lower bone part 4, which will also be referred to below as the tibia 4, and in an upper bone part 6, which will also be referred to below as femur 6. An end of a ligament that is to be fitted is fixedly secured to the bone part 4 in the vicinity of an opening 12 in the bone part 4, in a way which is known or yet to be developed. A securing element according to the invention, which is to be discussed below with reference to FIG. 2, is arranged substantially in the hole 10, in the vicinity of an opening 14 thereof. At this point, it should be noted that it is also possible to fixedly secure the ligament in the vicinity of the opening 14 and to arrange the securing element in the vicinity of the opening 12. Another option is to arrange a first securing element in the vicinity of the opening 12 in combination with a second securing element in the vicinity of the opening 14.

FIG. 2 shows a securing element 20 which comprises a first clamping part 22, a second clamping part 24, a stop nut 26, a spring 28, a tube 30, a ligament coupling element 32 in wire, thread or ribbon form, and a pulling element 34.

The first clamping part 22 is substantially annular and has an imaginary axis of rotational symmetry 36. The first clamping part 22 has a smooth surface on its outer circumference, although it may also be provided with a threaded profile or another suitable profile allowing the first clamping part 22 to be anchored in a hole 8 or 10. However, anchoring of this nature is not necessary. Furthermore, the first clamping part 22 bears a collar 38 or one or more substantially radially oriented projections which do not extend along the entire outer edge of the first clamping part 22, or other means, which are optionally flexibly connected to the first clamping part, with a similar function, to be described below, to the collar 38. The first clamping part 22 is provided on its inner side with a conical first surface 40 and an internal screw thread 42. The first surface 40 has a predetermined roughness.

The second clamping part 24 is a substantially frustoconical body which is provided with a central bore, the diameter of which changes in stepped fashion over its length, so as to define a section having a first, small diameter and a section having a second, large diameter. The tube 30 is fixedly secured in the section with the small diameter, while in the section with the large diameter the tube 30 defines a blind annular space in which a section of the spring 28 is accommodated. The conicity and dimensions of the outer surface 44 (also referred to as the second surface) of the second clamping part 24 substantially correspond to the conicity and dimensions of the first surface 40. The second surface 44 has a predetermined roughness.

The stop nut 26 is a substantially cylindrical body which is provided with an external screw thread 46, the dimensions of which substantially correspond to those of the internal screw thread 42. The stop nut 26 is also provided with through-bores 48 and 50. The stop nut 26 also comprises a groove 52.

The ligament coupling element 32 in the form of a flexible, wear-resistant element in wire, thread or ribbon form, which is preferably little or not stretchable, has been threaded through the bores 48 in order to form a loop on the side facing the first clamping part 22. As an alternative to the loop, the ligament coupling element 32 may also have two or a different number of ends, which means that the ligament coupling element may be formed from one or more elements in wire, thread or ribbon form.

The securing element 20 has a proximal side at the end where the stop nut 26 is provided, and a distal side located oppositely thereto.

As an alternative for the bores 48 in the stop nut 26, it is possible for bores with the same purpose, i.e. for guiding the ligament coupling element 32 towards the first surface 40 and the second surface 44, to be arranged in the first clamping part 22, in which case the path of the bores is indicated by a dashed line 49 in FIG. 2. Thus, a rotation of the stop nut 26 with respect to the first clamping part 22, as will be described in more detail below, has no influence on the position of the ligament coupling element 32.

The pulling element 34 in the form of a flexible element in wire, thread or ribbon form has been threaded through the bore 50 and through the tube 30, and is provided with a thickened portion, such as a button or other stop that is fixedly connected to the pulling element 34, on the side of the second clamping part 24 which faces the first clamping part 22. The pulling element can be shaped in various other ways, for example to be rigid and releasable, provided that its function (that of exerting a tensile force on the second clamping part 24) is retained.

During assembly of the securing element 20, the second clamping part 24 is placed in the first clamping part 22 in such a manner that the first surface 40 lies opposite the second surface 44, with sections of the ligament coupling element 32 being located between the first surface 40 and the second surface 44. Then, the stop nut 26 is screwed into the screw thread 42; by way of example, a screwdriver can be fitted into the groove 52. It is in this case advantageous to hold the stop nut 26 in a stationary position and to rotate the first clamping part 22, in order to prevent the ligament coupling element 32 from becoming twisted, which has an adverse effect on the functionality of the securing element 20. That end of the tube 30 which faces the stop nut 26 is guided within the bore 50, and introducing the stop nut 26 all the way to the end of the screw thread 42 will lead to a predetermined compression of the spring 28. As a result, the ligament coupling element 32 is securely clamped under a predetermined force between the first surface 40 and the second surface 44, thereby making it possible to determine the length of the loop-shaped section of the ligament coupling element 32. The conicity of the first surface 40 and the second surface 44 is selected in such a manner that exerting a tensile force on the loop-shaped section of the ligament coupling element 32 in the direction away from the securing element 20 (so at the distal side of the securing element 20) improves the clamping of the ligament coupling element between the first surface 40 and the second surface 44. When the pulling element 34 is pulled at the proximal side of the securing element 20, the second clamping element 24 can be displaced in the direction of the stop nut 26 with respect to the first clamping element 22; to do this, it is necessary to overcome the force provided by the spring 28. The clamping of the ligament coupling element 32 between the first clamping part 22 and the second clamping part 24 is eliminated as a result, so that the length of the loop-shaped section of the ligament coupling element 32 can be altered as desired. As soon as tensile force is subsequently no longer exerted on the pulling element 34, the spring 28 presses the second clamping part 24 back into a position in which the ligament coupling element 32 is clamped securely between the first surface 40 and the second surface 44.

The loop-shaped section of the ligament coupling element 32 can be coupled in a suitable way to a ligament 54 which is to be arranged in a patient's body, for example by enabling a loop formed from the ligament to engage in the loop-shaped section of the ligament coupling element 32, as illustrated by a dashed line in FIG. 2. However, the person skilled in the art will be able to conceive numerous other ways of effecting coupling between the loop-shaped section of the ligament coupling element 32 and a ligament 54, but this is not essential to the present invention and will therefore not be discussed here.

Figure 3:
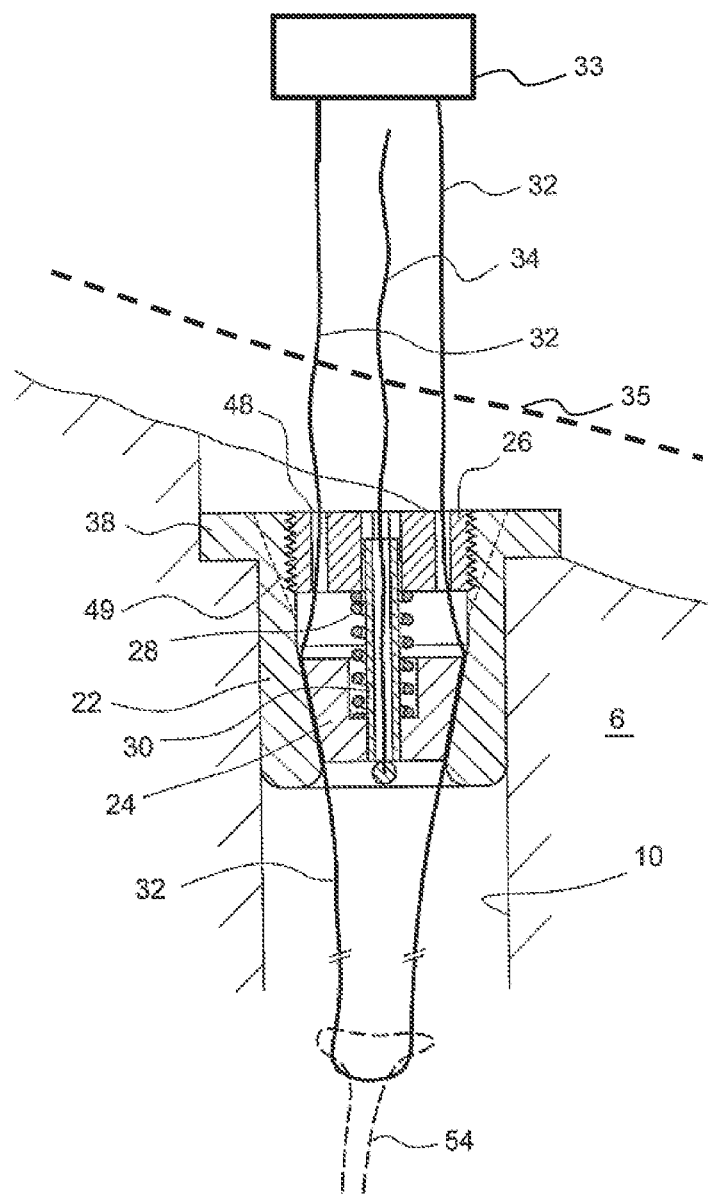
FIG. 3 shows the securing element according to FIG. 2 in an assembled form, provided in a human or animal body.

FIG. 3 shows the securing element 20 in an assembled condition, and mounted in a hole 10 in a bone part 6.

The following procedure can be adopted in an operation for fitting a ligament. The description below is based on the fitting of a ligament in a knee joint of a human or animal patient as illustrated in FIG. 1. The following steps are carried out:

Forming holes 8 and 10 in tibia 4 and femur 6, respectively.

(Optional). Arranging a pulling wire or pulling hook or a section of grasping forceps from the opening 12 through the holes 8 and 10 as far as beyond the opening 14.

Passing the loop-shaped section of ligament coupling element 32 of assembled securing element 20 from opening 14 towards and through opening 12.

Coupling prepared ligament to the loop-shaped section of the ligament coupling element 32 which projects out of the opening 12.

Figure 4:
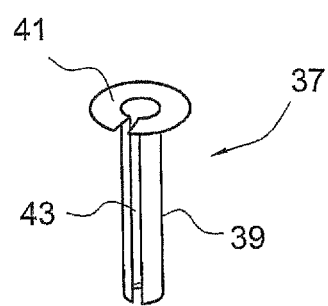
FIG. 4 shows a perspective view on a larger scale of a stop element.

Pulling ligament 54 through the hole 8 and into the hole 10 to a predetermined location, if appropriate using a stop element 37, which is shown in FIG. 4 and is to be introduced into the hole 10 from the opening 14. The stop element 37 comprises an elongate sleeve-like body 39 and a collar 41, which are both provided with a continuous slot 43. In use, a section of the ligament coupling element 32 is introduced into the body 39 via the slot 43, and the body 39 is introduced into the hole 10 until the collar 41 comes to a stop against the surface of the bone part 6. With the aid of the ligament coupling element 32, the ligament 54 is pulled into the hole 10 until the ligament comes to a stop against that end of the body 39 which faces away from the collar 41. The ligament 54 then adopts the desired position in the holes 8 and 10, the length of the body 39 being selected in such a manner that the securing element 20 which is subsequently to be fitted can function optimally. Then, the stop element 37 is removed.

(Optional) Fit securing element 20 via opening 14 into the hole 10, with the collar 38 of the first clamping part 22 being supported on the surface of the femur 6 and the remaining section of the first clamping part being located inside the hole 10. If appropriate, the collar 38 can be pivotably coupled to the first clamping part if the longitudinal direction of the hole 10 is not oriented perpendicular to the surface of the femur 6, or the hole 10 at the surface of the femur 6 can be adapted to engage the collar 38, as illustrated in FIG. 3. The length of the loop-shaped section of the ligament coupling element 32 is adjusted. The securing element 20 can optionally be fixedly connected to the wall of the hole 10.

Secure end(s) of the ligament 54 to the tibia 4 in the vicinity of the opening 12. Carry out the preceding step if this has not yet taken place.

(Preferred) Move joint into a predetermined position.

Couple ends of the ligament coupling element 32 which project out of the bores 48 at the proximal side of the securing element 20 to a force-measuring instrument 33, such as a spring balance, preferably outside the body of the patient, and set a predetermined tensile force (with the second clamping part 24 being able to be lifted with the aid of the pulling element 34 in order to release the clamping of the ligament coupling element 32 between the first surface 40 and the second surface 44). A mechanism which is not shown in more detail and only permits the application of a predetermined maximum force can be used to set the tensile force.

(Preferred) Record tensile force.

Release the second clamping part 24 in order to securely clamp sections of the ligament coupling element 32 between the first surface 40 and the second surface 44.

It should be noted that as an alternative to positioning the securing element 20 in the opening 14, another option is for it to be positioned in the opening 12 or for securing elements 20 to be arranged in both the opening 14 and the opening 12.

The opening in the skin 35 (indicated by a dashed line) which has been made at the location of the opening 14 for the purpose of fitting the ligament can then be closed, with the ends of the ligament coupling element 32 which project out of the bores 48 at the proximal side of the securing element 20, and also the pulling element 34 being arranged so as to protrude through the skin 35.

After a predetermined period of time, for example a few days or weeks, those ends of the ligament coupling element 32 which project out of the bores 48 are coupled to a force-measuring instrument 33 again, with the joint in a predetermined position which is determined for example externally with the aid of a trestle or in some other suitable way. After a predetermined force has been set, with the second clamping part 24 lifted with the aid of the pulling element 34 so as to release the clamping of the ligament coupling element 32 between the first surface 40 and the second surface 44, the second clamping part 24 is released in order to bring about secure clamping of sections of the ligament coupling element 32 between the first surface 40 and the second surface 44.

These operations of tensioning the ligament coupling element 32 (and thereby tensioning the implanted ligament 54) can if desired be repeated at least one more time if necessary. After these operations have been carried out for the last time, those ends of the ligament coupling element 32 which project out of the bores 48 can be cut off just above the skin 35 and moved under the skin, and the skin opening can be definitively closed.

It will be clear from the above that the securing element according to the invention provides the option of providing the correct tension in an implanted ligament during a surgery in a simple way with the aid of a measuring mechanism located outside the body, with the further possibility of restoring the correct tension if the ligament has become stretched a certain time after the surgery in a simple manner in the same way, and without an invasive surgery, from a place outside the body. The precise setting of the tension in the ligament is very important not only for the patient but also for research and statistical purposes.

Based on the principles disclosed above, the person skilled in the art will be able to employ alternative embodiments which are also within the scope of the appended claims.

The invention claimed is:

1. A method for connecting a ligament with a bone part of a human or animal patient under its skin, the method comprising:
   (a) providing a through channel in the bone part, the channel having a distal end and a proximal end;
   (b) providing a securing element comprising:
      i. a ligament coupling element, wherein the ligament coupling element is selected from the group consisting of a wire, a thread, and a ribbon, and wherein the ligament coupling element has ends;
      ii. a clamping element, comprising a first clamping part that has a first surface, and a second clamping part that has a second surface, wherein the first surface and the second surface face each other, and wherein the second clamping part is movable relative to the first clamping part between a first position in which the ligament coupling element is clamped between the first surface and the second surface, and a second position in which the ligament coupling element is free to move between the first surface and the second surface;
      iii. a pulling element connected to the second clamping part;
   (c) connecting the ligament coupling element with the ligament;
   (d) providing the ligament coupling element through the channel from the distal end to the proximal end, an end of the ligament coupling element protruding through the skin at the proximal end of the channel;
   (e) providing the ligament coupling element between the first and second surfaces;
   (f) connecting the first clamping part with the bone part, and coupling the second clamping part with the first clamping part, the pulling element protruding through the skin at the proximal end of the channel;
   (g) bringing the second clamping part in said first position by providing a first force acting between the first clamping part and the second clamping part;
   (h) while maintaining the first force acting between the first clamping part and the second clamping part, bringing the second clamping part in said second position by providing a second force on the pulling element overcoming the first force;
   (i) while maintaining the first force acting between the first clamping part and the second clamping part, while maintaining the second force on the pulling element overcoming the first force, and while maintaining the second clamping part in said second position, setting a tension in the ligament coupling element;
   (j) while maintaining the first force acting between the first clamping part and the second clamping part, removing the second force on the pulling element, to bring the second clamping part in said first position.

2. The method according to claim 1, wherein steps (h), (i) and (j) are repeated at least once after a predetermined time period.

3. The method of claim 2, wherein the time period is a few days.

4. The method of claim 2, wherein the time period is a few weeks.

5. The method of claim 1, wherein the first force is provided by a spring member.

6. A method for connecting a ligament with a bone part of a human or animal patient under its skin, the method comprising:
   (a) providing a skin opening for invasive surgery;
   (b) providing a through channel in the bone part, the channel having a distal end and a proximal end;
   (c) providing a ligament coupling element, wherein the ligament coupling element is selected from the group consisting of a wire, a thread, and a ribbon, and wherein the ligament coupling element has a loop-shaped section and at least one end;
   (d) providing a securing element at the proximal end of the channel in the bone part, the securing element being configured to readjustably secure the ligament coupling element to the bone part;
   (e) coupling the loop-shaped section of the ligament coupling element to the ligament at a distal side of the securing element;
   (f) providing the ligament coupling element through the channel;
   (g) coupling the ligament coupling element to the bone part with the securing element by clamping;
   (h) causing the at least one end of the ligament coupling element to protrude through the skin opening for invasive surgery, outside the body of the patient;
   (i) releasing the clamping of the securing element so as to release the ligament coupling element from the bone part and applying a tensioning force, using a first force-measuring instrument coupled to the at least one end of the ligament coupling element and located outside the body of the patient, on the at least one end of the ligament coupling element outside the body of the patient to adjust the length of the loop-shaped section of the ligament coupling element to set the ligament to a predetermined tension;
   (j) securely connecting the ligament coupling element to the bone part with the securing element;
   (k) releasing the tensioning force on the at least one end of the ligament coupling element outside the body of the patient;
   (l) closing said skin opening for invasive surgery, while causing the at least one end of the ligament coupling element to remain protruding, through the skin, outside the body of the patient during a predetermined time period;
   (m) after said predetermined time period, releasing the clamping of the securing element so as to release the ligament coupling element from the bone part and applying a new tensioning force, using a second force-measuring instrument coupled to the at least one end of the ligament coupling element and located outside the body of the patient, on the at least one end of the ligament coupling element protruding through the skin outside the body of the patient, without invasive surgery;
   (n) securely connecting the ligament coupling element to the bone part with the securing element by clamping;

(o) releasing the new tensioning force on the at least one end of the ligament coupling element outside the body of the patient; and (p) cutting the at least one end of the ligament coupling element off just above the skin and moving the cut end under the skin.

7. The method of claim 6, wherein the predetermined time period is between a surgery operation for introducing the ligament coupling element and a later stage.

8. The method of claim 6, wherein the time period is a few days.

9. The method of claim 6, wherein the time period is a few weeks.

10. The method of claim 6, wherein the first and second force-measuring instruments are the same.

11. A method for connecting a ligament with a bone part of a human or animal patient under its skin, the method comprising:

(a) providing a skin opening for invasive surgery;

(b) providing a through channel in the bone part;

(c) providing a ligament coupling element, wherein the ligament coupling element is selected from the group consisting of a wire, a thread, and a ribbon, and wherein the ligament coupling element has a loop-shaped section and at least one end;

(d) providing a securing element configured to readjustably secure the ligament coupling element to the bone part;

(e) coupling the loop-shaped section of the ligament coupling element to the ligament;

(f) providing the ligament coupling element through the channel;

(g) causing said at least one end of the ligament coupling element to protrude through the skin opening for invasive surgery, outside the body of the patient;

(h) applying a predetermined tensioning force, using a first force-measuring instrument coupled to said at least one end of the ligament coupling element and located outside the body of the patient, on said at least one end of the ligament coupling element protruding through said skin opening outside the body of the patient to set a first tension in the ligament coupling element;

(i) securely connecting a part of the ligament coupling element to the bone part with the securing element, said part of the ligament coupling element being located between said at least one end of the ligament coupling element and said loop-shaped section, to retain the first tension in a portion of the ligament coupling element extending between said part of the ligament coupling element and said loop-shaped section;

(j) releasing the predetermined tensioning force on said at least one end of the ligament coupling element outside the body of the patient, while the first tension in said portion of the ligament coupling element extending between said part of the ligament coupling element and said loop-shaped section is retained;

(k) closing said skin opening for invasive surgery, while causing the at least one end of the ligament coupling element to remain protruding, through the skin, outside the body of the patient during a predetermined time period after steps (a) to (j);

(l) during said predetermined time period, allowing a tension in said portion of the ligament coupling element extending between said part of the ligament coupling element and said loop-shaped section to decrease from said first tension to a second tension lower than said first tension;

(m) after said predetermined time period, releasing the secure connection between said part of the ligament coupling element and the bone part and applying a new tensioning force, using a second force-measuring instrument coupled to said at least one end of the ligament coupling element and located outside the body of the patient, on said at least one end of the ligament coupling element protruding, through said skin, outside the body of the patient, without invasive surgery;

(n) securely connecting said part of the ligament coupling element to the bone part with the securing element to set, based on said new tensioning force, a third tension higher than said second tension in said portion of the ligament coupling element extending between said part of the ligament coupling element and said loop-shaped section;

(o) releasing said new tensioning force on said at least one end of the ligament coupling element protruding through the skin, outside the body of the patient, while the third tension in said portion of the ligament coupling element extending between said part of the ligament coupling element and said loop-shaped section is retained; and (p) cutting said at least one end of the ligament coupling element off just above the skin, and moving the cut end under the skin.

12. The method of claim 11, wherein the predetermined time period is between a surgery operation for introducing the ligament coupling element and a later stage.

13. The method of claim 11, wherein the time period is a few days.

14. The method of claim 11, wherein the time period is a few weeks.

15. The method of claim 11, wherein the first and second force-measuring instruments are the same.

* * * * *